(12) United States Patent
Kovacsne-Mezei et al.

(10) Patent No.: US 7,589,100 B2
(45) Date of Patent: Sep. 15, 2009

(54) NON-HYGROSCOPIC AND POWDERY AMORPHOUS PIMECROLIMUS

(75) Inventors: Adrienne Kovacsne-Mezei, Debrecen (HU); Csilla Nemethne Racz, Tiszavasvári (HU); Judith Aronhime, Rehovot (IL); Csaba Szabo, Debrecen (HU); Viktor Gyollai, Debrecen (HU); Sandor Molnar, Debrecen (HU); Micahel Pinchasov, Rishon-Lezion (IL)

(73) Assignee: TEVA Gyógyszergyár Zártkörún Müködö Részvénytársaság, Debrecen (HU)

( * ) Notice: Subject to any disclaimer, the term of this patent is extended or adjusted under 35 U.S.C. 154(b) by 0 days.

(21) Appl. No.: 11/293,283

(22) Filed: Dec. 1, 2005

(65) Prior Publication Data

US 2006/0147540 A1    Jul. 6, 2006

Related U.S. Application Data

(60) Provisional application No. 60/632,372, filed on Dec. 1, 2004, provisional application No. 60/633,926, filed on Dec. 6, 2004, provisional application No. 60/641,697, filed on Jan. 5, 2005, provisional application No. 60/641,868, filed on Jan. 5, 2005, provisional application No. 60/641,869, filed on Jan. 5, 2005, provisional application No. 60/662,440, filed on Mar. 16, 2005, provisional application No. 60/705,681, filed on Aug. 3, 2005, provisional application No. 60/709,160, filed on Aug. 17, 2005.

(51) Int. Cl.
   C07D 498/18    (2006.01)
   A61K 31/395   (2006.01)
   A61P 17/00    (2006.01)

(52) U.S. Cl. ...................... 514/291; 540/456

(58) Field of Classification Search .................. 540/456; 514/291

See application file for complete search history.

(56) References Cited

U.S. PATENT DOCUMENTS 3,244,592 A    4/1966   Arai et al.
6,423,722 B1 *  7/2002   Dosenbach et al. ......... 514/291
6,620,325 B2   9/2003   Fuenfschilling et al.
6,706,727 B1   3/2004   Fleissner et al.

FOREIGN PATENT DOCUMENTS

| EP | 0 323 865 A1 | 7/1989 |
|---|---|---|
| EP | 0 427 680 A1 | 5/1991 |
| EP | 0 427 680 B1 | 5/1991 |
| EP | 0 480 623 A1 | 4/1992 |
| EP | 1 234 833 A2 | 8/2002 |
| WO | WO 93/04679 A1 | 3/1993 |
| WO | WO-93/04680 A1 | 3/1993 |
| WO | WO 93/18050 A1 | 9/1993 |
| WO | WO-99/01458 A1 | 1/1999 |
| WO | WO-01/90110 A1 | 11/2001 |
| WO | WO 03/063821 A2 | 8/2003 |
| WO | WO 03/063822 A2 | 8/2003 |
| WO | WO 2004/089958 A2 | 10/2004 |
| WO | WO 2005/010015 A1 | 2/2005 |
| WO | WO 2005/117837 A1 | 12/2005 |
| WO | WO 2006/031664 A1 | 3/2006 |

OTHER PUBLICATIONS

Griffiths, C.E., "Ascomycin: An Advance in the Management of Atopic Dermatitis." *British Journal of Dermatology*, (2001) vol. 144, p. 679-681.

Kessler, H., et al., "Structure of Rapamycin: An NMR and Molecular-Dynamics Investigation" Helvetica Chimica Acta, (1993) vol. 76, p. 117-130.

Brittain, H.G. (Editor) "Polymorphism in Pharmaceutical Solids" Drugs and the Pharmaceutical Sciences vol. 95, (1999) Marcel Dekker, Inc. New York, New York.

Remington, J. P. (Editor) "The Science and Practice of Pharmacy", vol. II, Chapter 92, "Oral Solid Dosage Forms", p. 1615-1649 (1995) Mack Publishing Company, Easton, Pennsylvania.

Yu, L: "Amorphous Pharmaceutical Solids: Preparation, Characterization and Stabilization." Advanced Drug Delivery Reviews, (2001) vol. 48, p. 27-42.

* cited by examiner

*Primary Examiner*—Bruck Kifle
(74) *Attorney, Agent, or Firm*—Kenyon & Kenyon LLP (57) ABSTRACT

An amorphous pimecrolimus and processes for providing an amorphous pimecrolimus are provided.

38 Claims, 10 Drawing Sheets

NON-HYGROSCOPIC AND POWDERY AMORPHOUS PIMECROLIMUS

RELATED APPLICATIONS

This application claims benefit of U.S. Provisional Patent Applications Nos. 60/632,372, filed Dec. 1, 2004, 60/633,926, filed Dec. 6, 2004, 60/641,697, filed Jan. 5, 2005, 60/641,868, filed Jan. 5, 2005, 60/641,869, filed Jan. 5, 2005, 60/662,440, filed Mar. 16, 2005, 60/705,681, filed Aug. 3, 2005, and 60/709,160, filed Aug. 17, 2005, the contents of which are incorporated herein in their entirety by reference.

FIELD OF INVENTION

The present invention relates to amorphous pimecrolimus and methods of preparing amorphous pimecrolimus. The invention especially includes amorphous pimecrolimus characterized by properties selected from: powdery and non-hygroscopic.

BACKGROUND OF THE INVENTION

Pimecrolimus is an anti-inflammatory compound derived from the macrolactam natural product ascomycin, produced by certain strains of *Streptomyces*.

ASCOMYCIN

PIMECROLIMUS

Pimecrolimus is sold in the United States under the brand name ELIDEL®, and is approved for use against atopic dermatitis. The systematic name of pimecrolimus is (1R,9S,12S,13R,14S,17R,18E,21S,23S,24R,25S,27R)-12-[(1E)-2-{(1R,3R,4S)-4-chloro-3-methoxycyclohexyl}-1-methylvinyl]-17-ethyl-1,14-dihydroxy-23,25-dimethoxy-13,19,21,27-tetramethyl-11,28-dioxa-4-aza-tricyclo[22.3.1.0$^{4,9}$]octacos-18-ene-2,3,10,16-tetraone.

Pimecrolimus is the 32 epichloro derivative of ascomycin. Its empirical formula is $C_{43}H_{68}ClNO_{11}$, and its molecular weight is 810.47.

Many pharmaceutical solids can exist in different physical forms. Polymorphism is often characterized as the ability of a drug substance to exist as two or more crystalline phases that have different arrangements and/or conformations of the molecules in the crystalline lattice. Amorphous solids consist of disordered arrangements of molecules, and do not possess a distinguishable crystal lattice.

Polymorphs of a pharmaceutical solid may have different physical and solid-state chemical (reactivity) properties. These polymorphs differ in internal solid state structure, and, therefore, possess different chemical and physical properties, including packing, thermodynamic, spectroscopic, kinetic, interfacial, and mechanical properties. These properties can have a direct impact on drug product quality/performance, including stability, dissolution, and bioavailability.

The most stable polymorphic form of a drug substance is often used in a formulation because it has the lowest potential for conversion from one polymorphic form to another. On the other hand, metastable (a form other than the most stable form) and even amorphous forms may be chosen to enhance the bioavailability of the drug product. An amorphous form, being a disorganized solid mass, does not need to lose crystal structure before dissolution in the gastric juices, and, thus, often has greater bioavailability than a crystalline form.

Even if an amorphous form is desirable for formulation, its preparation on industrial scale is often problematic. Many processes used to prepare the amorphous form of an active pharmaceutical ingredient are not suitable for industrial scale production. In POLYMORPHISM IN PHARMACEUTICAL SCIENCES, DRUGS AND THE PHARMACEUTICAL SCIENCES, Vol. 95, the authors survey various processes for preparation of amorphous forms, and list solidification of melt, reduction of particle size, spray-drying, lyophilization, removal of a solvent from crystalline structure, precipitation of acids and bases by change in pH, and others such techniques employed to obtain the amorphous form of an active pharmaceutical ingredient.

Many of these processes however are not practical on an industrial scale. For example, to obtain an amorphous active pharmaceutical ingredient by solidification of melt, the active pharmaceutical ingredient has to be heated beyond its melting point, which may require expenditure of much energy, particularly when the active pharmaceutical ingredient has a high melting point. Further, the high temperatures may chemically damage the active pharmaceutical ingredient.

Another one of these processes, lyophilization, is quite expensive on large scale, and generally has limited capacity. Furthermore, lyophilization with an organic solvent is often dangerous since it presents a fire hazard.

According to Remington: THE SCIENCE AND PRACTICE OF PHARMACY, 19$^{th}$ Ed., vol. II, pg. 1627, spray-drying consists of bringing together a highly dispersed liquid and a sufficient volume of hot air to produce evaporation and drying of the liquid droplets. Spray-drying however is often limited to aqueous solutions unless special expensive safety measures are taken. Also, in spite of the short contact time, certain undesirable physical and chemical characteristics of the emerging solids are in particular cases unavoidable. The turbulence present in a spray-drier as a result of the moving air may alter the product in an undesirable manner. Modifications to the spray-drying technique are disclosed in WO 03/063821 and WO 03/063822.

European Patent EP 427 680 B1 discloses a method of synthesizing amorphous pimecrolimus (Example 66a). The method yields amorphous pimecrolimus as a colorless foamy resin.

U.S. Pat. No. 6,423,722 discloses crystalline forms of pimecrolimus, such as form A, form B, etc. U.S. '722 also contend that by performing example 66a from the European Patent EP 427 680 B 1, amorphous pimecrolimus is obtained.

However, there is a need for methods of preparing amorphous pimecrolimus that is characterized as non-hygroscopic and/or powdery. There is also a need for methods of preparing such amorphous pimecrolimus preferably using techniques and equipment suitable for industrial scale preparation. The present invention provides such methods.

SUMMARY

In one embodiment, the present invention provides an amorphous pimecrolimus characterized by properties selected from: powdery and non-hygroscopic. Preferably, the amorphous pimecrolimus is powdery. More preferably, the powdery amorphous pimecrolimus is non-hygroscopic.

In another embodiment, the present invention provides a powdery and non-hygroscopic amorphous pimecrolimus.

In one embodiment, the present invention provides a process for preparing powdery amorphous pimecrolimus by a fast evaporation process comprising dissolving pimecrolimus in a solvent selected from the group consisting of: acetone, methanol, ethanol, toluene, acetonitrile, di-isopropyl-ether, and ethyl acetate, feeding the solution into a chamber maintained at a reduced pressure and a temperature of less than about 100° C. until obtaining a precipitate, and grinding the precipitate until obtaining a powder.

In another embodiment, the present invention provides a process for preparing powdery amorphous pimecrolimus, comprising grinding a product or an obtained product, of amorphous pimecrolimus, to obtain a powder.

In yet another embodiment, the present invention provides a process for preparing powdery amorphous pimecrolimus by spray-drying.

In one embodiment, the present invention provides a process for preparing powdery amorphous pimecrolimus comprising combining a solution of pimecrolimus in a polar organic solvent with water, followed by drying.

In another embodiment, the present invention provides a pharmaceutical composition comprising a therapeutically effective amount of the powdery amorphous pimecrolimus and a pharmaceutically acceptable excipient or carrier.

In another embodiment the present invention provides a method for treating a patient suffering from atopic dermatitis, comprising the step of administering to the patient the pharmaceutical formulation described above.

DETAILED DESCRIPTION OF THE INVENTION

As used herein, the term "product" or "obtained product" refers to a substance that is neither liquid nor gaseous.

As used herein, the term "non-hygroscopic" refers to a compound that contains no more than about 2% wt/wt of water, more preferably no more than about 1.5% wt/wt of water, most preferably no more than about 1% wt/wt of water, when exposed to 80% humidity, at room temperature for 1 week.

As used herein, the terms "powder" or "powdery" refer to a solid compound in the form of particles or granules where the particles or granules can be poured. Preferably, the powders are solid, loose, dry particles.

As used herein, the term "spray-drying" broadly refers to processes involving breaking up liquid mixtures into small droplets, preferably, by atomization, and rapidly removing solvent from the mixture. In a typical spray-drying apparatus, there is a strong driving force for evaporation of solvent from the droplets, which may be provided by a heated drying gas. Spray-drying processes and equipment are described in Perry's CHEMICAL ENGINEER'S HANDBOOK, pgs. 20-54 to 20-57 (Sixth Edition 1984).

By way of non-limiting example only, the typical spray-drying apparatus comprises a drying chamber, an atomizer for atomizing a solvent containing feed into the drying chamber, a source of heated drying gas that flows into the drying chamber to remove solvent from the atomized solvent containing feed, an outlet for the products of drying, and a product collector, located downstream of the drying chamber. Examples of such apparatuses include Niro Models PSD-1, PSD-2, and PSD-4 (Niro A/S, Soeborg, Denmark). Typically, the product collector includes a cyclone connected to the drying apparatus. In the cyclone, the particles produced during spray-drying are separated from the drying gas and evaporated solvent, allowing the particles to be collected. A filter may also be used to separate and collect the particles produced by spray-drying. The process of the invention is not limited to the use of such drying apparatuses as described above.

As used herein, the term "amorphous" in reference to pimecrolimus, refers to pimecrolimus containing less than about 5 percent crystalline forms, preferably less than about 3 percent, and, more preferably, less than about 1 percent, as measured as area percentage of peaks present in a PXRD.

As used herein, the term "vacuum" refers to a reduced pressure of below about 100 mm Hg, more preferably, below about 50 mm Hg, and, most preferably, below about 30 mm Hg.

As used herein, the term "reduced pressure" refers to a pressure below 760 mm Hg or 1 atmosphere.

As used herein, the term "therapeutically effective amount" means the amount of the amorphous pimecrolimus of the present invention that, when administered to a patient for treating a disease or other undesirable medical condition, is sufficient to have a beneficial effect with respect to that disease or condition. The "therapeutically effective amount" will vary depending on the disease or condition and its severity, and the age, weight, etc., of the patient to be treated. Determining the therapeutically effective amount is within the ordinary skill of the art, and requires no more than routine experimentation.

In one embodiment, the present invention provides an amorphous pimecrolimus characterized by properties selected from: powdery and non-hygroscopic. Preferably, the amorphous pimecrolimus is powdery. More preferably, the powdery amorphous pimecrolimus is non-hygroscopic.

In another embodiment, the present invention provides a powdery and non-hygroscopic amorphous pimecrolimus.

Figure 1:
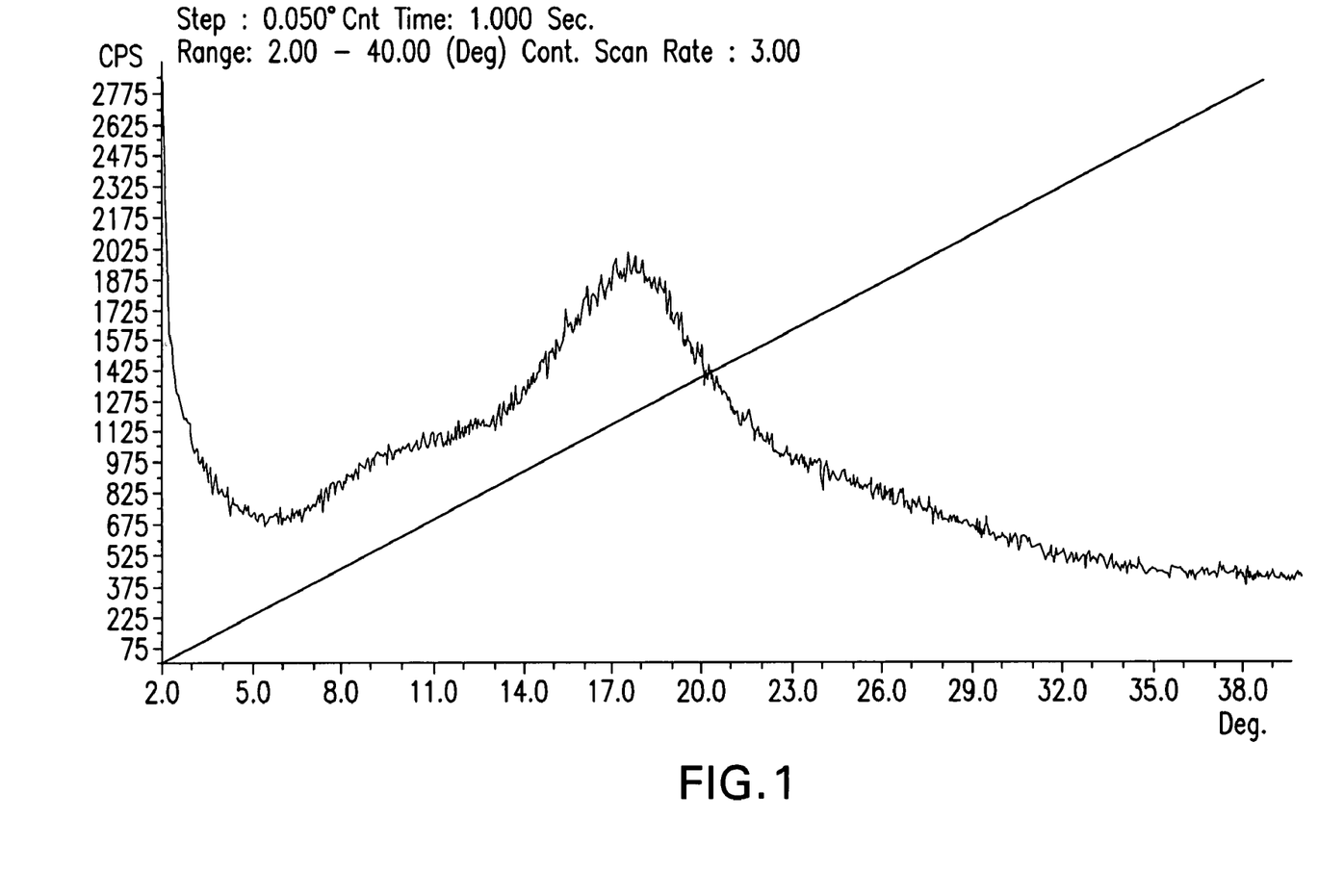
FIG. 1 illustrates a PXRD pattern of the amorphous pimecrolimus produced by grinding.

The PXRD pattern of the amorphous pimecrolimus of the present invention is shown in FIG. 1. The absence of peaks in the PXRD indicates that the amorphous pimecrolimus of the present invention lacks detectable crystalline material. The PXRD shown in FIG. 1 has the ability to detect about 1 percent to 5 percent crystalline forms of pimecrolimus. Thus, the sample of amorphous pimecrolimus of the present invention tested contained less than about 5 percent crystalline forms of pimecrolimus.

Figure 2A:
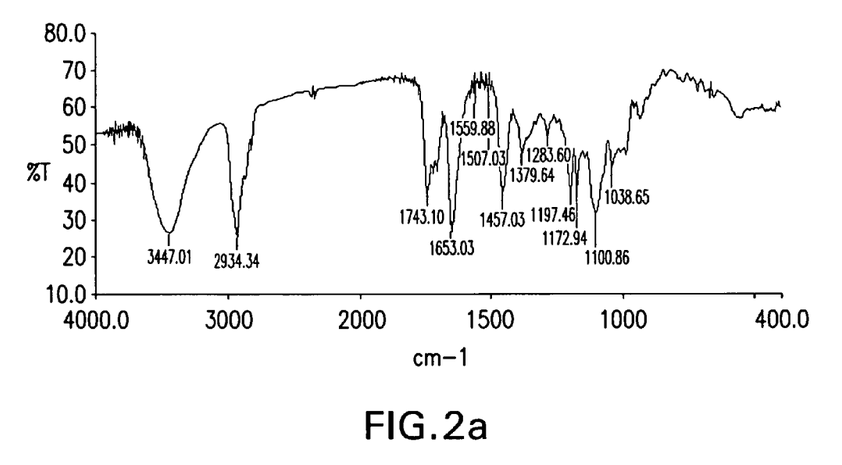
FIG. 2a illustrates FT-IR spectrum of amorphous pimecrolimus in KBr pellet.
Figure 2B:
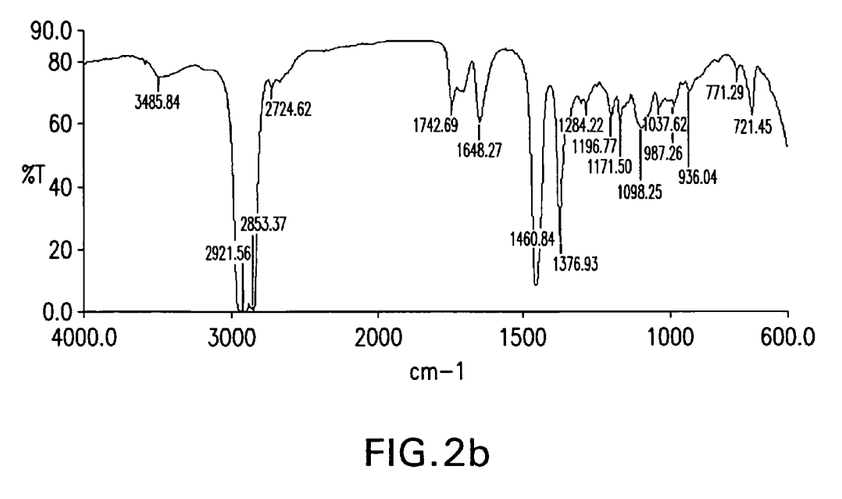
FIG. 2b illustrates FT-IR spectrum amorphous pimecrolimus in mineral oil.

The amorphous pimecrolimus of the present invention can be characterized by FT-IR spectroscopy by peaks at 2934, 2826, 1743, 1718, 1700, 1653, 1457, 1380, 1284, 1197, 1173, 1101, 1039, 988, 937, and 773 $cm^{-1}$. The amorphous pimecrolimus of the present invention can be further characterized by FT-IR spectroscopy by peaks at 2725, 1743, 1648, 1284, 1197, 1172, 1098, 1038, 987, 936, 771, and 721 $cm^{-1}$. FIGS. 2a and 2b show the FT-IR spectra of amorphous pimecrolimus of the present invention.

Figure 3:
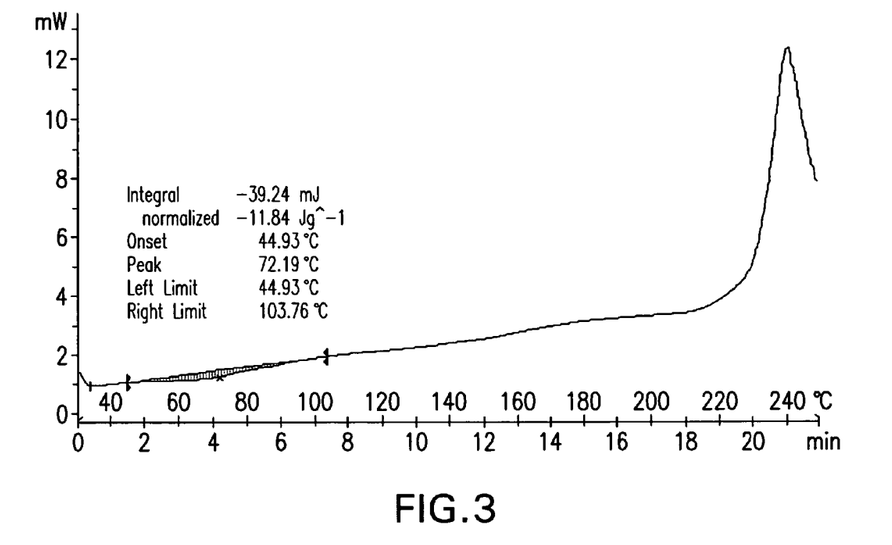
FIG. 3 illustrates DSC curve of the amorphous pimecrolimus.
Figure 4:
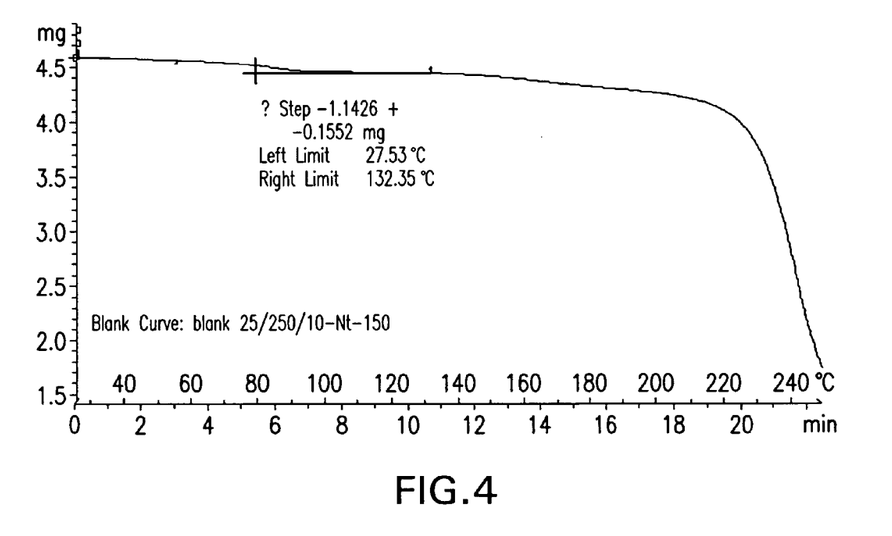
FIG. 4 illustrates TGA curve of the amorphous pimecrolimus.
Figure 5:
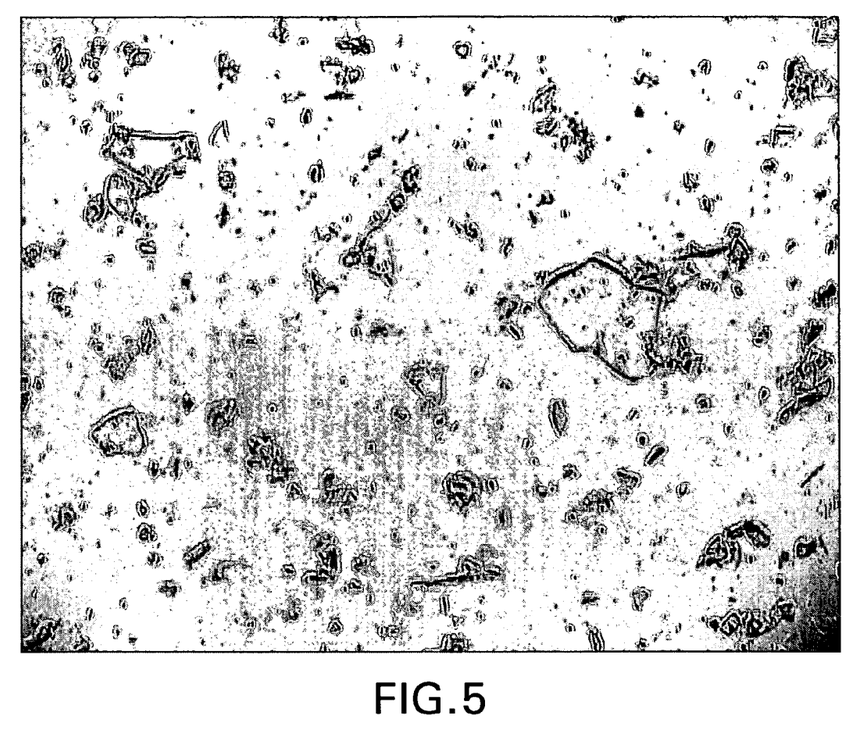
FIG. 5 illustrates irregular plate-shaped particles of amorphous pimecrolimus.

FIG. 3 shows the characteristic differential scanning calorimetry (DSC) curve of the amorphous pimecrolimus of the present invention. The small and broad endotherm up to 100° C. indicates the presence of small quantities of water, and the exotherm above 220° C. indicates decomposition. The absence of sharp endotherms indicates absence of crystalline material. Based on thermogravimetric analysis (TGA) measurements, the weight loss was 1 percent. The water content by Karl Fisher analysis was 0.8 percent. A representative TGA curve of amorphous pimecrolimus is provided in FIG. 4.

The powdery amorphous pimecrolimus may have plate-shaped particles.

The hygroscopicity of amorphous pimecrolimus of the present invention was examined by measuring the water content in samples stored at different relative humidity value (RH) (0, 40, 60, and 80 percent) for a period of one week. Table 1 shows the results.

TABLE 1

Pimecrolimus LOD values (%) v. relative humidity

| RH (%) | (i) | LOD (%) | (ii) |
|---|---|---|---|
| Original | (iii) | 1.1 | (iv) |
| 0 | (v) | 0.8 | (vi) |
| 20 | (vii) | — | (viii) |
| 40 | (ix) | 1.1 | (x) |

TABLE 1-continued

Pimecrolimus LOD values (%) v. relative humidity

| RH (%) | (i) | LOD (%) | (ii) |
|---|---|---|---|
| 60 | (xi) | 1.1 | (xii) |
| 80 | (xiii) | 1.1 | (xiv) |

The water content of the samples stored at a relative humidity of from about 0 percent to about 80 percent remained unchanged at about 1 percent. This demonstrates that the amorphous pimecrolimus of the present invention is non-hygroscopic.

The non-hygroscopic amorphous pimecrolimus of the present invention is advantageous with respect to its use in pharmaceutical compositions. This is especially important, as it is well known that amorphous materials are generally hygroscopic.

In one embodiment, the present invention provides a process for preparing powdery amorphous pimecrolimus by a fast evaporation process comprising dissolving pimecrolimus in an organic solvent selected, feeding the solution into a chamber maintained at a reduced pressure and a temperature of less than about 100° C. until obtaining a precipitate and grinding the precipitate until obtaining a powder. Preferably, the solvent is selected from the group consisting of: $C_1$ to $C_4$ alcohols, $C_3$ to $C_7$ ketones, $C_3$ to $C_7$ esters, $C_5$ to $C_7$ straight or cyclic saturated hydrocarbons or $C_2$ to $C_8$ ethers and mixtures thereof. More preferably, the solvent is selected from the group consisting of: methanol, ethanol, acetone, toluene, acetonitrile, ethyl acetate, heptane, hexane, diethyl ether, methyl isobutyl ether, di-isopropyl-ether and mixtures thereof. Most preferably, the solvent is selected from the group consisting of: methanol and acetone.

The fast evaporation process of the present invention allows amorphous pimecrolimus to form rapidly when pimecrolimus is dried by rapid evaporation from a suitable solvent under reduced pressure. The main driving force of the evaporation is a combination of temperature/reduced pressure, and not a hot air flow as in spray-drying. The authors of POLYMORPHISM IN PHARMACEUTICAL SCIENCES, DRUGS AND THE PHARMACEUTICAL SCIENCES, Vol. 95, do not list the fast evaporation process of the present invention as one employed to produce amorphous forms.

While other drying techniques may be suitable for laboratory scale, such as less than about 100 grams, the fast evaporation process of the present invention allows for preparing amorphous pimecrolimus on an industrial scale, i.e., a batch of at least about 500 grams, more preferably, at least about 1 Kg, and, most preferably, at least about 10 Kg.

The concentration of the pimecrolimus solution, solvent type, temperature, vacuum level, and feeding rate are set to a combination where the pimecrolimus, coming from the inlet, such as a nozzle, precipitates instantly. Otherwise crystalline material can also form. The specific conditions may vary. However, generally the process may be carried out at a temperature below about 100° C., a reduced pressure, and a concentrated solution of the pimecrolimus in a solvent, preferably having a concentration of more than about 20 percent m/m, and/or concentrated to the point of saturation (solution in equilibrium with a solid solute), and a flow rate of about 10 to about 50 $cm^3$/hour/inlet. These combinations should allow for evaporation of the solvent at the given conditions, i.e., below the vapor pressure of the solvent.

The technique is in principle applicable both for aqueous and organic solvents. However the preferred use is with organic solvents since organic solvents are generally more volatile. Preferred solvents are the easily volatile organic solvents with relatively low boiling point as described above. Preferably, technical grades of these solvents are used containing less than about 20 percent water, more preferably less than about 2 percent water by volume. The boiling point of the solvent is preferably below about 100° C., more preferably below about 70° C., under atmospheric pressure at room temperature.

The process of the present invention is carried out optimally with a concentrated solution of pimecrolimus. The pimecrolimus solution, typically having a pimecrolimus concentration of more than about 20 percent m/m, preferably, about 20 percent to about 80 percent m/m, more preferably about 60 percent to about 75 percent, and, most preferably, a saturated solution is fed into a reduced pressure chamber, at a temperature of less than about 100° C., through at least one inlet, preferably, a nozzle or nozzles. The solution may be fed into the chamber using a pressure differential between the source of the solution and the chamber, which may be created by a pump, pressure from another tank, reduced pressure or vacuum in the drying chamber, pressure from a syringe device, or any tubes that has a diameter which is small enough to enable fast evaporation of the concentrated solution introduced to the chamber under vacuum. The chamber may be any reactor, flask, or container capable of maintaining the desirable process conditions, such as reduced pressure.

In the fast evaporation process of the present invention, the solution is added dropwise or continuously to the drying chamber. One skilled in the art would appreciate that the speed of the addition of the solution will depend on the solvent used, the viscosity of the mixture, and the height of the chamber. The rate of flow of the solution, if delivered through a nozzle, is preferably in the range of about 10 to about 50 $cm^3$/hour/nozzle (inlet), depending on the concentration of the pimecrolimus solution, pressure, temperature, and properties of the solvent.

The conditions in the chamber are preferably such that a drop of solution explodes substantially instantaneously in the chamber in a manner similar to a popcorn kernel popping. This solidification preferably occurs substantially spontaneously, as the solution is introduced into the chamber from the inlet or nozzle, and does not require any further action, such as stirring. The substantially instant evaporation provides a phase change from the solution to the solid before the solution contacts the bottom of the chamber when fed from the top. It will be recognized by those of ordinary skill in the art that it is possible to feed the solution from the side or bottom of the chamber as well.

When the solution reaches the drying chamber, the solvent evaporates substantially instantly, while the dissolved pimecrolimus precipitates as a sponge, i.e., a solid foam, or possibly as a solid. When the sponge mass reaches a certain mass, it falls to the bottom of the drying chamber. Alternatively, the solid may fall as it comes out of the nozzle.

The number of inlets for the nozzles in the drying chamber depends on the capacity of vacuum. Vapor removal from the drying chamber can be accelerated by a small flow of an inert gas, preferably nitrogen. The drying equipment preferably contains a stirrer, which is suitable to break the solid, forming a powder.

After breaking the solid, drying can be continued under reduced pressure, preferably with stirring, until the residual solvent concentration declines to the required FDA level. The solvent level depends on the type of solvent, but is preferably no more than about 5000 ppm, more preferably, no more than about 4000 ppm, and, most preferably, no more than about 3000 ppm. The powder is preferably dried after stirring under reduced pressure, i.e., at less than 1 atmosphere pressure, more preferably, at a pressure of less than about 100 mm Hg, and, most preferably, at a pressure less than about 50 mm Hg. The temperature is preferably about 30° C. to about 50° C., and, more preferably, about 35° C. to about 45° C. The powder is preferably dried for about 1 hour to about 10 hours. The powder can be discharged from the dryer in a conventional manner, for example via an outlet located at the bottom of the chamber, while the stirrer is rotating. A valve may be opened to discharge the powder, and additional force, in addition to gravitational force, may be used to accelerate the discharge.

Preferably, the feeding system used with the fast evaporation process of the present invention has a distributor syringe/nozzle diameter of less than about 3 mm, and more preferably, less than about 2 mm. A representative pilot scale distributor is illustrated in FIG. 8, and a representative industrial feeding system is illustrated in FIG. 10. The pimecrolimus solution is preferably feed continuously into a chamber having a working pressure of less than about 760 mm Hg, preferably, less than about 100 mm Hg, more preferably, less than about 50 mm Hg, and, most preferably, less than about 20 mm Hg, at a working temperature of less than about 100° C., preferably, about 20° C. to about 80° C., and, more preferably, about 25° C. to about 45° C. Optionally, the pimecrolimus solution is feed into a drying chamber with a stirrer and a discharge device with a flow of inert gas, such as nitrogen, $N_2$. While a drop-wise addition is possible, scaling up to an industrial scale is facilitated with a syringe and a continuous feed.

A simple apparatus for use in the fast evaporation process of the present invention comprises a round-bottom flask and an inlet, such as a nozzle or a syringe through a septum into the interior of the flask, where the flask can be evacuated to provide a vacuum, such as that illustrated in FIG. 7. The inlet of the apparatus provides for introduction of the pimecrolimus solution, and is preferably positioned at the top or side of the chamber, but may also be positioned at the bottom of the chamber. As illustrated in FIG. 7, the left opening of the apparatus is closed to allow for vacuum generation. The left intake may also be used to feed inert gas to create a substantially dry environment. In addition to a place for injection, the apparatus has an outlet to a vacuum pump, aspirator, or other device for providing a vacuum. The apparatus may optionally comprise a heater, a discharge, and/or a stirrer.

In the process of the invention, a sample of the solid from the chamber may be taken and tested for quality assurance. For example, if the process results in pimecrolimus, having more than about 5 percent crystalline material as area percentage by PXRD, and less than 5 percent crystallinity is desired, the process may be changed by manipulating the conditions, for example, temperature, vacuum, flow rate, solution concentration, solvent, etc. If highly pure amorphous pimecrolimus is desired, pimecrolimus having more than about 5 percent crystallinity may be discarded, or can be recycled in the process. Batches with a crystallinity of less than about 5 percent may then be chosen. In some instances, a crystallinity of less than about 3 percent or less than about 1 percent may be desired. The presence of amorphous pimecrolimus may be detected by a lack of peaks in a PXRD pattern or by a lack of a melting point in a DSC thermogram. The area under the peaks in a PXRD pattern may be used in order to determine the degree of crystallinity in the pimecrolimus, and whether the pimecrolimus is amorphous, as desired.

In another embodiment, the present invention provides a process for preparing powdery amorphous pimecrolimus, comprising grinding a product or an obtained product, of amorphous pimecrolimus, to obtain a powder. Optionally, the grinding is done by using a pestle.

In yet another embodiment, the present invention provides a process for preparing a powdery amorphous pimecrolimus comprising spray-drying a solution of pimecrolimus in a solvent. Preferably, the resulting pimecrolimus is non-hygroscopic.

Figure 6:
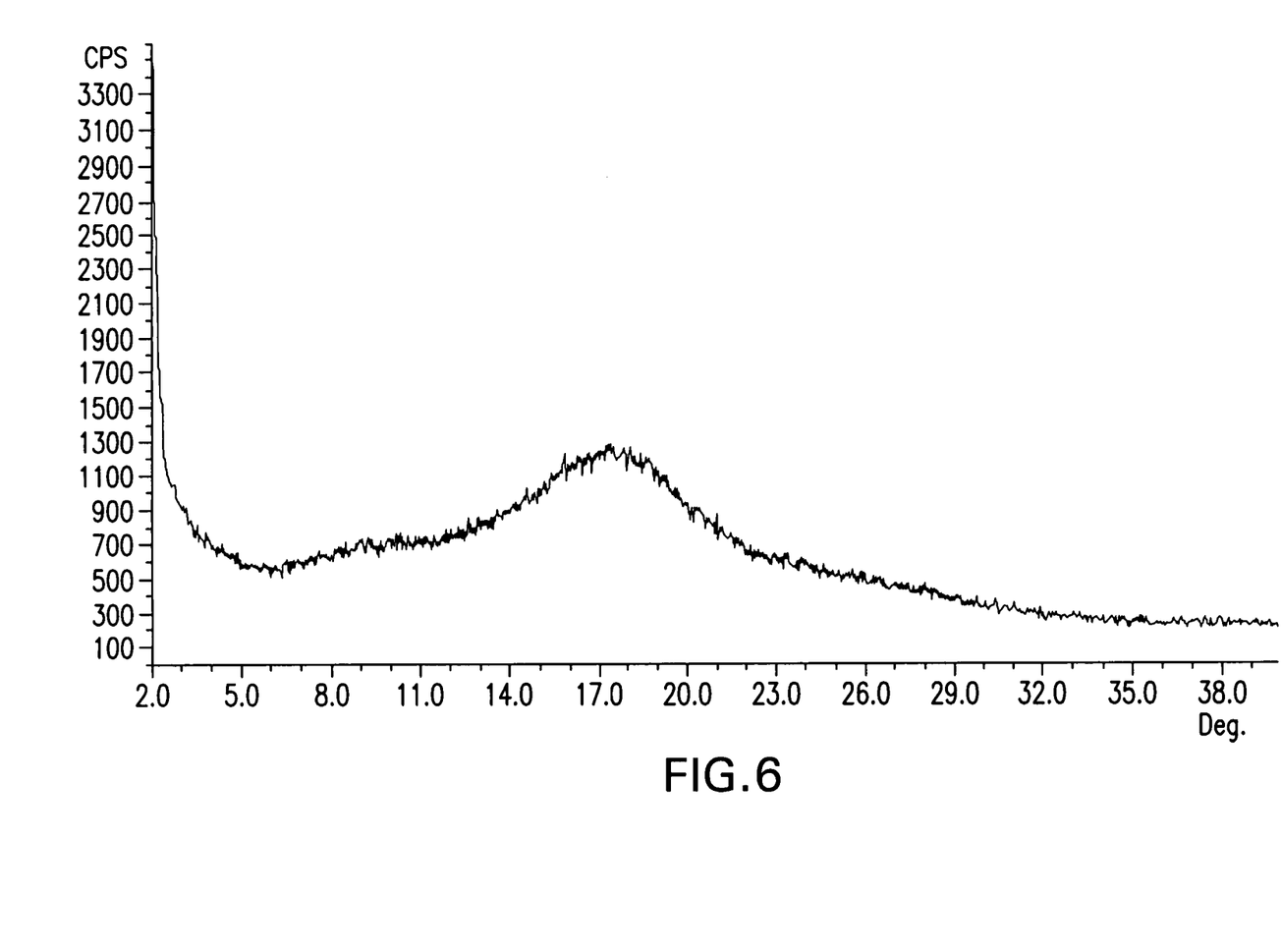
FIG. 6 illustrates PXRD pattern of the amorphous pimecrolimus produced by spray-drying.
Figure 7:
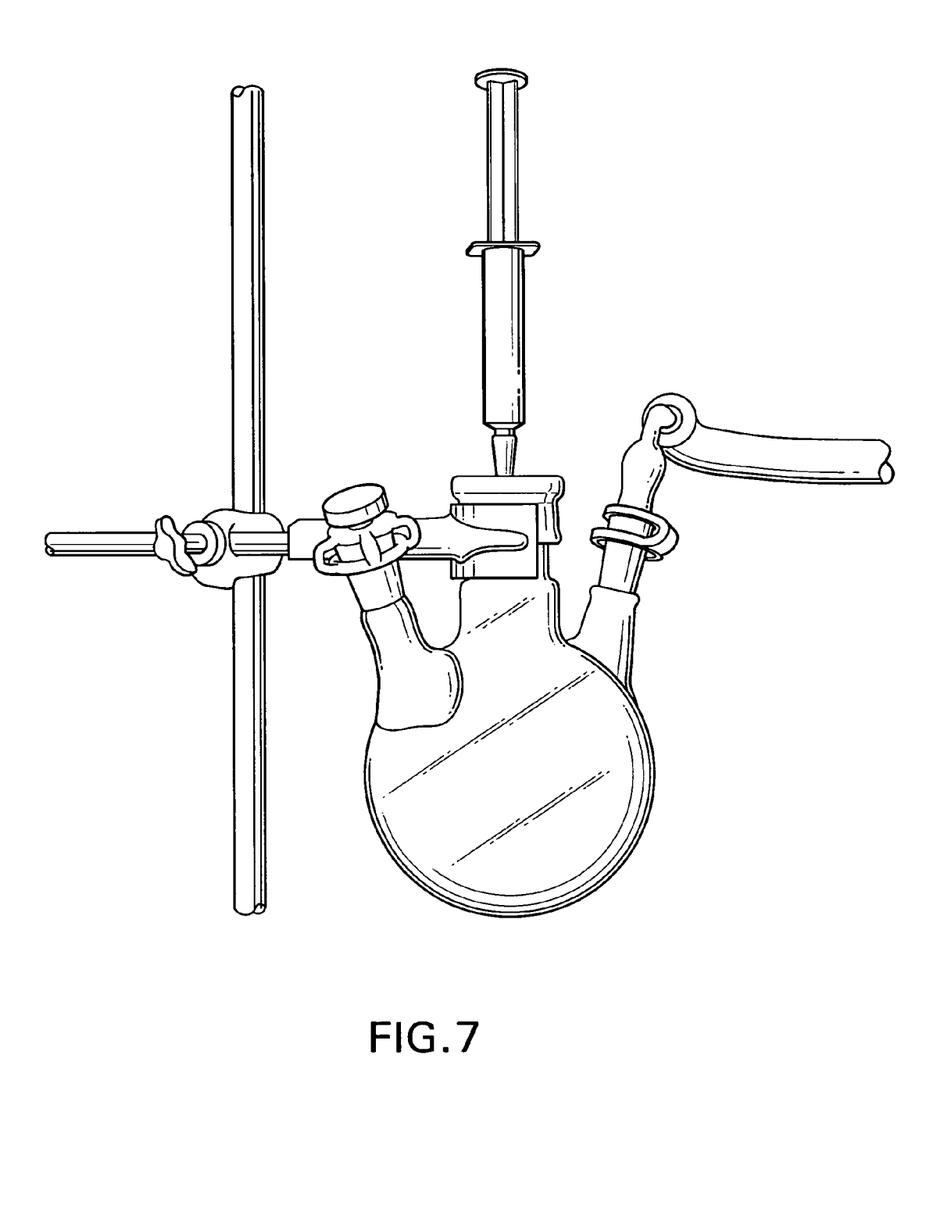
FIG. 7 illustrates illustration of a laboratory construction for instant drying by fast evaporation.
Figure 8:
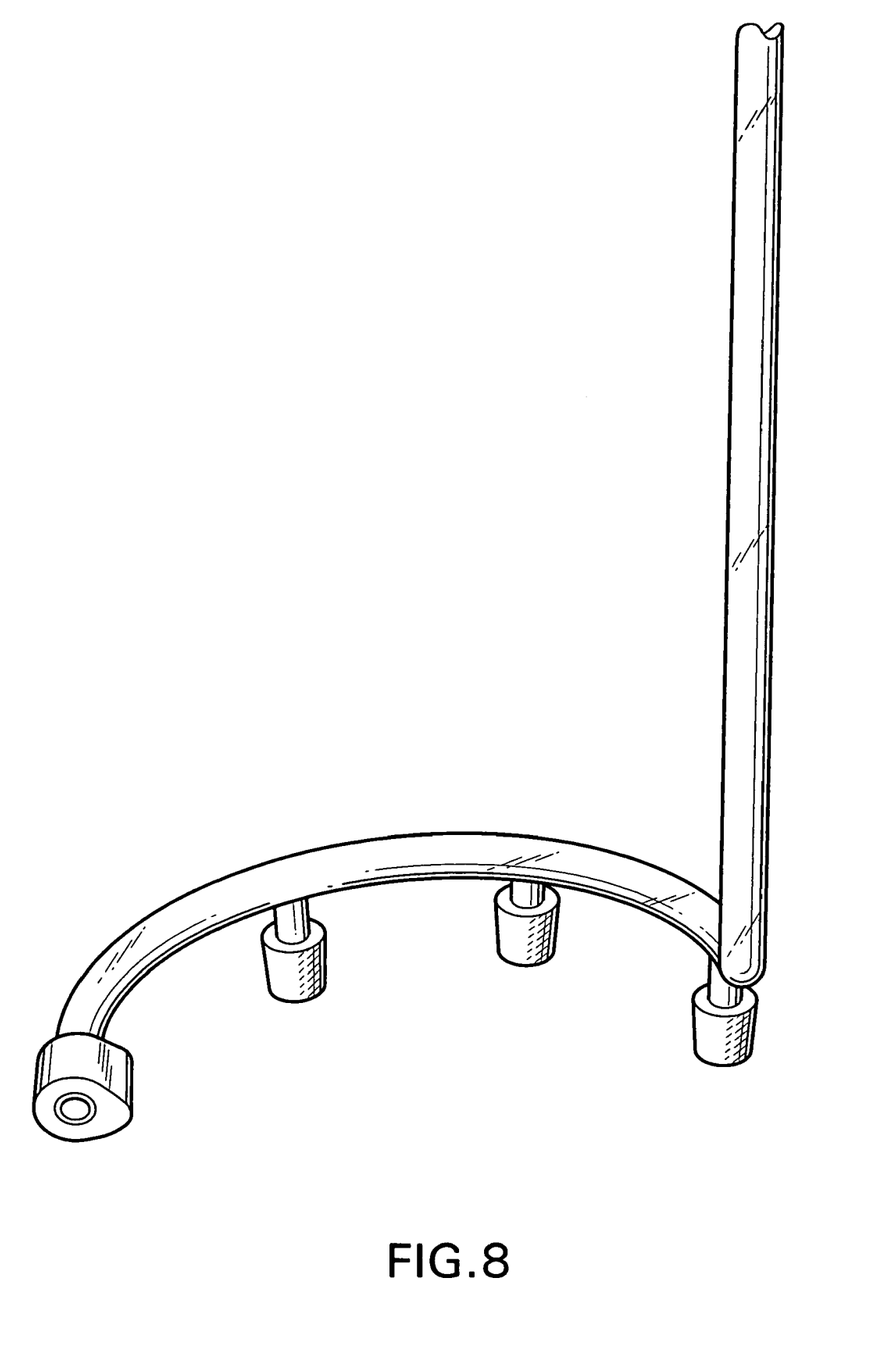
FIG. 8 illustrates illustration of a distributor in pilot scale.
Figure 9:
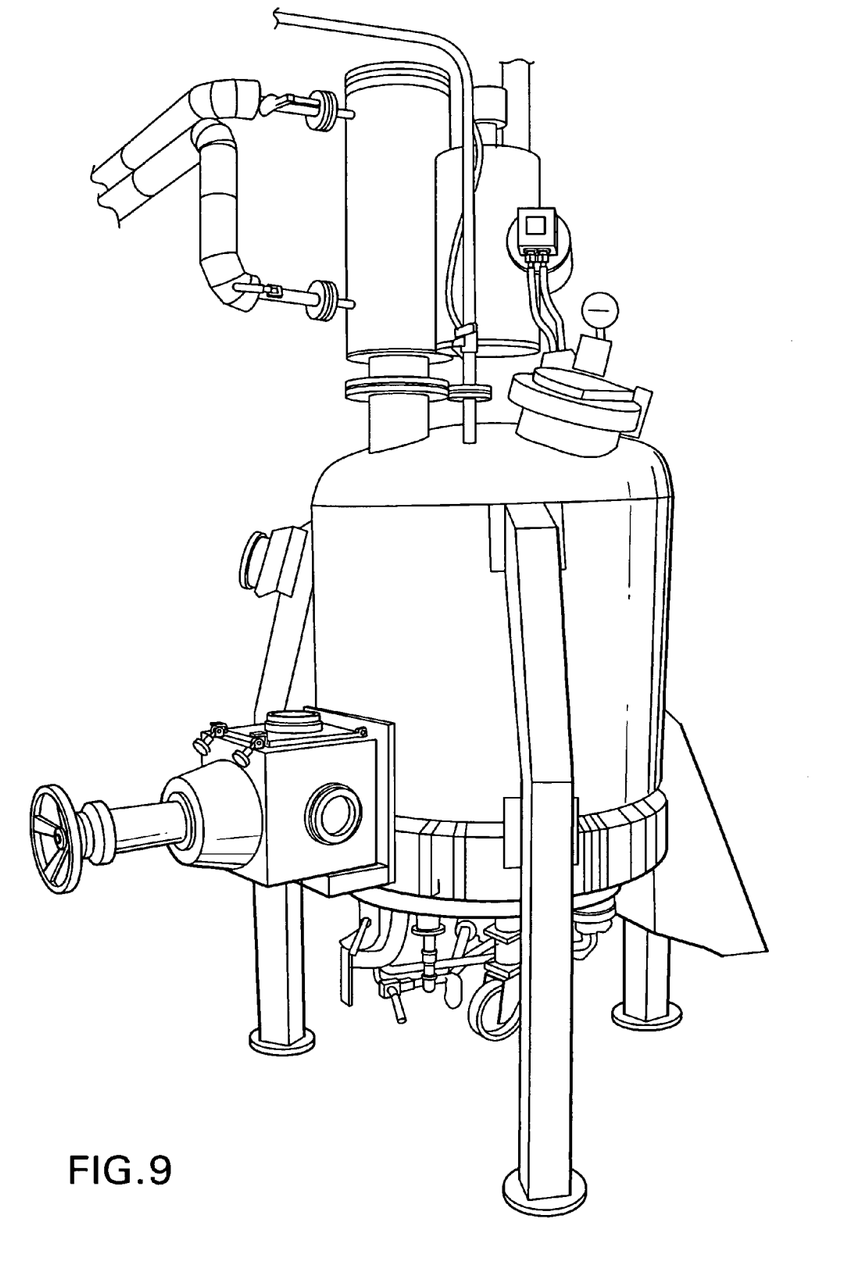
FIG. 9 illustrates illustration of an industrial dryer.
Figure 10:
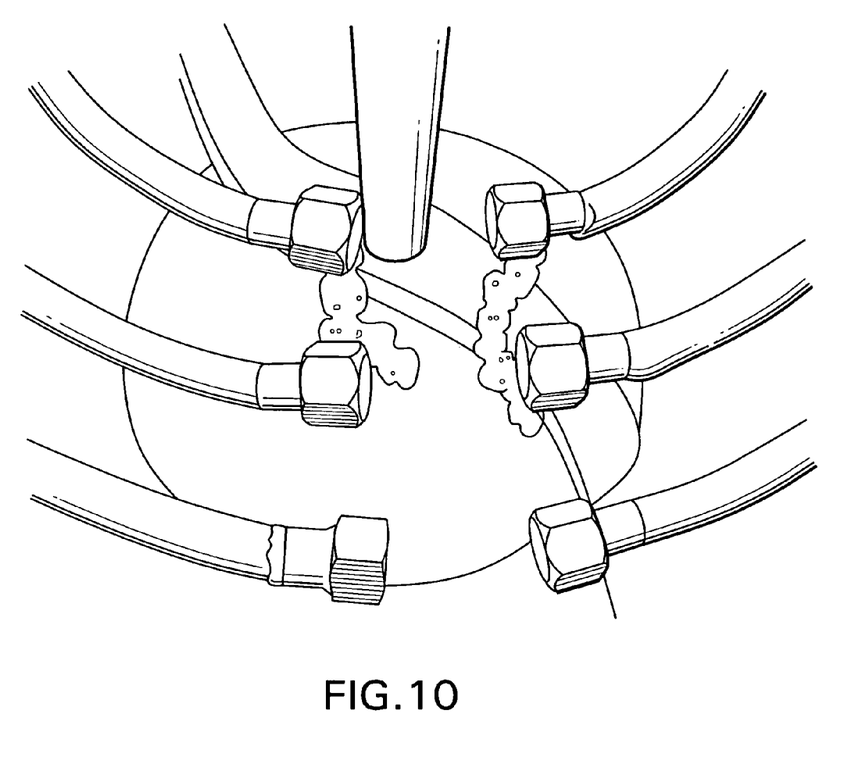
FIG. 10 illustrates illustration of an industrial feeding system for fast evaporation, forming a precipitated solid as a sponge.
Figure 11:
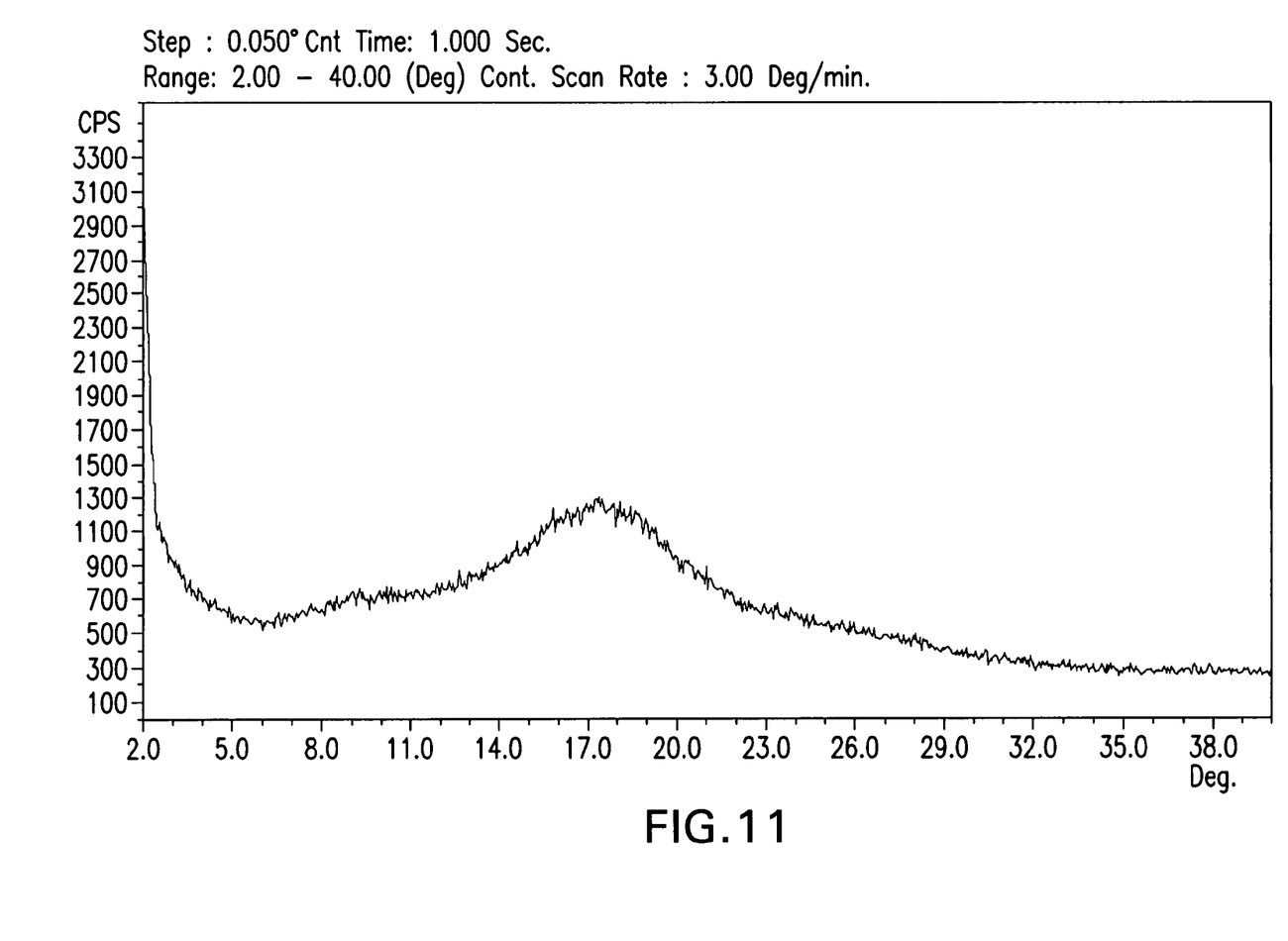
FIG. 11 illustrates PXRD pattern of spray-dried pimecrolimus.

Preferably, the pimecrolimus is dissolved in a solvent selected from the group consisting of: acetone, methanol, ethanol, toluene, acetonitrile, di-isopropyl-ether, and ethyl acetate. Preferably, the solution is relatively concentrated, i.e., at least about 25 percent (w/w), more preferably, at least about 40 percent (w/w), and, most preferably, at least about 50 percent (w/w). The solution is pumped into a spray-dryer that contains a drying gas. Preferably, the solution is pumped into a spray-dryer at room temperature. Preferably, the drying gas is an inert drying gas, such as nitrogen. Preferably, the spray-dryer has an inlet temperature of less than about 100° C., and, more preferably, a temperature of about 50° C. When the solution is introduced into the drying gas, the solvent evaporates, resulting in amorphous pimecrolimus. A representative spray-dryer is illustrated in FIG. 9. The evaporated solvent and drying gas are removed from the spray-drier, and the resulting amorphous pimecrolimus is recovered. PXRD patterns obtained from spray-drying pimecrolimus in accordance with the invention are illustrated in FIGS. 6 and 11. The illustrated PXRD patterns are free of any crystalline peaks, demonstrating that the pimecrolimus is amorphous.

In one embodiment, the present invention provides a process for preparing powdery amorphous pimecrolimus comprising combining a solution of pimecrolimus in a polar organic solvent with water, followed by drying. Preferably, the resulting pimecrolimus is non-hygroscopic. This method is suitable for industrial scale production, and requires only common techniques and equipment. Preferably, the polar organic solvent is selected from the group consisting of: $C_1$-$C_4$ nitriles, $C_1$-$C_4$ ethers, $C_1$-$C_4$ ketones, and $C_1$-$C_4$ alcohols that are miscible with water. More preferably, the polar organic solvent is selected from the group consisting of: isopropanol, tetrahydrofuran (THF), acetone, and methyl-THF. Preferably, the pimecrolimus solution is added dropwise into the water. Preferably, the volume of water is larger than the volume of pimecrolimus solution added, usually by a factor of at least about 5, more preferably, by a factor of at least about 10, more preferably, by a factor of at least about 50, and most preferably, by a factor of at least about 100. Preferably, the pimecrolimus solution is added to the water at room temperature, and the mixture formed then cooled. Preferably, the mixture is cooled to about 5° C. Preferably, the cooled mixture is maintained for about one hour. Optionally, the cooled solution is stirred. Preferably, the obtained amorphous pimecrolimus is filtered, washed with water, dried, and examined for amorphous content, e.g., by PXRD. Preferably, the resulting amorphous pimecrolimus is in the form of a flowable powder.

In another embodiment, the present invention provides a pharmaceutical composition comprising a therapeutically effective amount of the powdery amorphous pimecrolimus and a pharmaceutically acceptable excipient or carrier.

Pharmaceutical compositions of the present invention preferably comprise one or more excipients or carriers. Excipients and carriers are added to the formulation for a variety of purposes.

Diluents may be added to the compositions of the present invention. Diluents increase the bulk of a solid pharmaceutical composition, and may make a pharmaceutical dosage form containing the composition easier for the patient and care giver to handle. Diluents for solid compositions include, for example, microcrystalline cellulose (e.g., AVICEL®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol, and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g., carbopol), carboxymethylcellulose sodium, dextrin, ethyl cellulose, gelatin, guar gum, hydrogenated vegetable oil, hydroxyethyl cellulose, hydroxypropyl cellulose (e.g., KLUCEL®), hydroxypropyl methyl cellulose (e.g., METHOCEL®), liquid glucose, magnesium aluminum silicate, maltodextrin, methylcellulose, polymethacrylates, povidone (e.g., KOLLIDON®, PLASDONE®), pregelatinized starch, sodium alginate, and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g., AC-DI-SOL®, PRIMELLOSE®), colloidal silicon dioxide, croscarmellose sodium, crospovidone (e.g., KOLLIDON®, POLYPLASDONE®), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB®), and starch.

Glidants can be added to improve the flowability of a non-compacted solid composition, and to improve the accuracy of dosing. Excipients that may function as glidants include colloidal silicon dioxide, magnesium trisilicate, powdered cellulose, starch, talc, and tribasic calcium phosphate.

When a dosage form, such as a tablet, is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion, and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance, and/or facilitate patient identification of the product and unit dosage level.

The present invention is not intended to encompass true solutions of pimecrolimus where the physical characteristics of the amorphous pimecrolimus of the present invention (good flowability, non-hygroscopicity, plate-shaped particles, etc.) are lost. However, the use of the amorphous pimecrolimus of the present invention to prepare such solutions (e.g., so as to deliver pimecrolimus in a liquid pharmaceutical formulation) is considered to be within the contemplation of the invention.

In liquid pharmaceutical compositions prepared using the amorphous pimecrolimus of the present invention, pimecrolimus and any other solid excipients are dissolved or suspended in a liquid carrier, such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions may also contain a viscosity enhancing agent to improve the mouth-feel of the product, and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents, such as sorbitol, saccharin, sodium saccharin, sucrose, aspartame, fructose, mannitol, and invert sugar, may be added to improve the taste.

Preservatives and chelating agents, such as alcohol, sodium benzoate, butylated hydroxyl toluene, butylated hydroxyanisole, and ethylenediamine tetraacetic acid, may be added at levels safe for ingestion to improve storage stability.

A liquid composition may also contain a buffer, such as gluconic acid, lactic acid, citric acid or acetic acid, sodium guconate, sodium lactate, sodium citrate, or sodium acetate. Selection of excipients and the amounts used may be readily determined by the formulation scientist based upon experience and consideration of standard procedures and reference works in the field.

The solid compositions of the present invention include powders, granulates, aggregates, and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form, and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs. Dosage forms also include creams and ointments. In particular, a cream comprising about 1 percent (w/w) of the amorphous pimecrolimus of the present invention is preferred. In such a cream, the excipients used are preferably benzyl alcohol, cetyl alcohol, citric acid, mono- and di-glycerides, oleyl alcohol, propylene glycol, sodium cetostearyl sulfate, sodium hydroxide, stearyl alcohol, triglycerides, and/or water.

The oral dosage form of the present invention is preferably in the form of an oral capsule having a dosage of about 10 mg to about 160 mg, more preferably from about 20 mg to about 80 mg, and most preferably capsules of 20, 40, 60, and 80 mg. Daily dosages may include 1, 2, or more capsules per day.

The dosage form of the present invention may be a capsule containing the composition, preferably a powdered or granulated solid composition of the invention, within either a hard or soft shell. The shell may be made from gelatin and, optionally, contain a plasticizer, such as glycerin and sorbitol, and an opacifying agent or colorant.

A composition for tableting or capsule filling may be prepared by wet granulation. In wet granulation, some or all of the active ingredients and excipients in powder form are blended, and then further mixed in the presence of a liquid, typically water, that causes the powders to clump into granules. The granulate is screened and/or milled, dried, and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet, and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray-dried lactose, dicalcium phosphate dihydrate, and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting; however, they are not subjected to a final tableting step.

The active ingredient and excipients may be formulated into compositions and dosage forms according to methods known in the art.

Although it is preferable that the compositions of the present invention contain the amorphous pimecrolimus of the present invention as the only form of pimecrolimus, it is not necessary. The amorphous pimecrolimus of the present invention may be used in pharmaceutical formulations or compositions as a mixture together with other forms of pimecrolimus (e.g., crystalline forms). However, it is preferred that the pharmaceutical formulations or compositions of the present invention contain 25-100 percent by weight, especially 50-100 percent by weight, of amorphous pimecrolimus of the present invention, based on the total amount of pimecrolimus in the formulation or composition. Preferably, such an amount of the amorphous pimecrolimus of the present invention is 75-100 percent by weight, especially 90-100 percent by weight. Highly preferred is an amount of 95-100 percent by weight.

Another embodiment of the present invention is a method for treating a patient suffering from atopic dermatitis, or another inflammatory disease, comprising the step of administering to the patient a pharmaceutical composition comprising a therapeutically effective amount of the amorphous pimecrolimus of the present invention.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

EXAMPLES

Experimental

X-Ray powder diffraction data can be obtained by methods known in the art using a SCINTAG® powder X-ray diffractometer model X'TRA® equipped with a solid state detector. Copper radiation of 1.5418 Å can be used. A round aluminum sample holder with round zero background quartz plate can be used, with a cavity having a diameter of 25 mm and a depth of 0.5 mm. The resolution of the X-ray diffractometers known in the art are in the range of 2 to 40 degrees two theta. DSC, TGA, and FT-IR measurements can be carried out by methods well known in the art.

Example 1

Preparation of Amorphous Pimecrolimus by Fast Evaporation

A 2 g sample of crude pimecrolimus was dissolved in 20 ml of acetone. The solution was treated with charcoal (CECA CXV), and evaporated to a volume of 1.5 ml (57 m/v percent). The solution was injected through a syringe needle (inner diameter of 0.6 mm) into a flask under a 10 to 20 mbar vacuum, heated by a 50° C. water bath. Pimecrolimus solidified instantly, and was collected in the bottom of the flask. The solid foam of pimecrolimus was maintained an additional one hour in the flask under vacuum. Then the pressure was equalized, and the solid was harvested and crushed. The pimecrolimus powder was dried in a vacuum oven at 50° C. overnight. The yield of amorphous pimecrolimus was 1.39 g or 69.5 percent. A PXRD analysis demonstrated that the product was pure, amorphous pimecrolimus. Residual solvent was analyzed by GC, and found to be acetone at 10 ppm.

Example 2

Preparation of Amorphous Pimecrolimus by Fast Evaporation

The experiment procedure according to Example 1 was followed, except ethyl acetate was used as the solvent, Norit SX1 was used as the activated charcoal, and the product was dried in a vacuum oven at 60° C. The yield of pimecrolimus was 1.49 g or 74.5 percent. A PXRD demonstrated that the product was pure, amorphous pimecrolimus. Residual ethyl acetate was analyzed by GC, and found to be 4640 ppm.

Example 3

Preparation of Amorphous Pimecrolimus by Precipitation

A 17.9 g sample of pimecrolimus was dissolved in 40.3 ml of isopropanol. The solution was slowly dropped into 1790 of water in small portions, i.e., dropwise, at room temperature. The mixture was cooled to 5° C. for an hour, and stirred at that temperature for an hour. The product was filtered and washed with water. The product was dried under reduced pressure at 60° C. overnight. A PXRD demonstrated that the product was amorphous pimecrolimus.

Example 4

Preparation of Amorphous Pimecrolimus by Precipitation

A 2 g sample of pimecrolimus was dissolved in 4 ml of THF. The resulting solution was slowly added to 200 ml of water in small portions, i.e., dropwise, at room temperature. The mixture was cooled to 5° C. for an hour, and stirred at that temperature for an hour. The product was filtered, and washed with water. The product was dried under reduced pressure at 60° C. overnight, and found to be amorphous.

Example 5

Preparation of Powdery Amorphous Pimecrolimus by Grinding

A 200 mg sample of sticky foamy pimecrolimus was ground gently in an agate mortar using a pestle for half a minute. The resulting pimecrolimus was powdery.

Example 6

Preparation of Amorphous Pimecrolimus by Spray-Drying

A 17.1 g toluene solution of pimecrolimus was spray-dried with a Buchi Mini Spray-dryer B-290. The pimecrolimus toluene solution, having a concentration of 51±4 percent (w/w) was pumped into the spray-dryer at room temperature, containing nitrogen as a drying gas at an inlet temperature of 50° C. The evaporated solvent and nitrogen exited the spray-drier at 36° to 37° C., resulting in 2.8 g of pimecrolimus. The pimecrolimus was analyzed with PXRD, resulting in an PXRD pattern free of any crystalline peaks, demonstrating that the pimecrolimus was amorphous.

Example 7

Preparation of Amorphous Pimecrolimus by Precipitation 19.5 g purified pimecrolimus (colorless resin) was dissolved in 217 ml acetone at 40° C. and concentrated. Residue: 38.76 g. The residue was diluted with 6 ml distilled water with stirring. Finally 1 ml acetone was added. This solution was added slowly to 2 L chilled distilled water that was stirred efficiently. After the addition had been completed, the suspension was stirred 20 min at 0° C. Then the solid was filtered and dried at 45° C. in vacuum oven overnight. Product: 15.65 g yellowish solid. Amorphous (XRD, DSC).

Example 8

Preparation of Amorphous Pimecrolimus by Grinding

Procedure of grinding: 200 mg of Pimecrolimus sample was ground gently in an agate mortar using a pestle for half a minute.

While it is apparent that the invention disclosed herein is well calculated to fulfill the objects stated above, it will be appreciated that numerous modifications and embodiments may be devised by those skilled in the art. Therefore, it is intended that the appended claims cover all such modifications and embodiments that fall within the true spirit and scope of the present invention.

What is claimed:

1. An amorphous pimecrolimus characterized by a powder X-ray diffraction pattern that is substantially free of any crystalline peaks, wherein the amorphous pimecrolimus is powdery.

2. The amorphous pimecrolimus of claim 1, wherein the powdery amorphous pimecrolimus is non-hygroscopic.

3. The amorphous pimecrolimus of claim 1, having a water content of less than about 1.5 percent (w/w).

4. The amorphous pimecrolimus of claim 3, having a water content of less than about 1 percent (w/w).

5. A process for preparing the powdery amorphous pimecrolimus of claim 1 by a fast evaporation process comprising
dissolving pimecrolimus in a solvent selected from the group consisting of acetone, methanol, ethanol, toluene, acetonitrile, di-isopropyl-ether, and ethyl acetate;
feeding the solution into a chamber maintained at a reduced pressure and at a temperature of less than about 100° C. until a precipitate is obtained; and
grinding the precipitate until a powder is obtained.

6. The process of claim 5, wherein the chamber has at least one inlet at a pressure of less than about 760 mm Hg and a temperature of below about 100° C.

7. The process of claim 6, wherein the inlet is a nozzle.

8. The process of claim 5, wherein the solution has a concentration of more than about 20 percent (w/w).

9. The process of claim 8, wherein the solution has a concentration from about 20 percent to about 80 percent (w/w).

10. The process of claim 9, wherein the solution has a concentration from about 60 percent to about 75 percent (w/w).

11. The process of claim 10, wherein the solution is a saturated solution.

12. The process of claim 5, wherein feeding the solution comprises feeding the solution at a flow rate of about 10 to about 50 cm$^3$/hour/inlet.

13. A process for preparing the powdery amorphous pimecrolimus of claim 1, comprising grinding a product or an obtained product, of amorphous pimecrolimus, to obtain a powder.

14. A process for preparing the powdery amorphous pimecrolimus of claim 1 comprising spray-drying a solution of pimecrolimus in a solvent.

15. The process of claim 14, wherein the solvent is selected from the group consisting of: acetone, methanol, ethanol, toluene, acetonitrile, di-isopropyl-ether, and ethyl acetate.

16. The process of claim 14, wherein the solution has a concentration of at least about 25 percent (w/w).

17. The process of claim 16, wherein the solution has a concentration of at least about 40 percent (w/w).

18. The process of claim 17, wherein the solution has a concentration of at least about 50 percent (w/w).

19. The process of claim 14, wherein the solution is pumped into a spray-dryer that contains a drying gas.

20. The process of claim 19, wherein the solution is pumped into the spray-dryer at room temperature.

21. The process of claim 19, wherein the drying gas is an inert drying gas.

22. The process of claim 19, wherein the spray-dryer has an inlet temperature of less than about 100° C.

23. The process of claim 22, wherein the spray-dryer has an inlet temperature of less than about 50° C.

24. A process for preparing the powdery amorphous pimecrolimus of claim 1 comprising combining a solution of pimecrolimus in a polar organic solvent with water, followed by drying.

25. The process of claim 24, wherein the polar organic solvent is selected from the group consisting of: $C_1$-$C_4$ nitrites, $C_1$-$C_4$ ethers, $C_1$-$C_4$ ketones, and $C_1$-$C_4$ alcohols that are miscible with water.

26. The process of claim 25, wherein the polar organic solvent is selected from the group consisting of: isopropanol, tetrahydrofuran (THF), acetone, and methyl-THF.

27. The process of claim 24, wherein the pimecrolimus solution is added dropwise into the water.

28. The process of claim 24, wherein the volume of water is larger than the volume of pimecrolimus solution added by a factor of at least about 5.

29. The process of claim 28, wherein the volume of water is larger than the volume of pimecrolimus solution added by a factor of at least about 10.

30. The process of claim 29, wherein the volume of water is larger than the volume of pimecrolimus solution added by a factor of at least about 50.

31. The process of claim 30, wherein the volume of water is larger than the volume of pimecrolimus solution added by a factor of at least about 100.

32. The process of claim 24, wherein the pimecrolimus solution is added to the water at room temperature to obtain a reaction mixture.

33. The process of claim 32, wherein the reaction mixture of pimecrolimus solution and water is cooled to about 5° C.

34. The process of claim 33, wherein the cooled reaction mixture is maintained for about one hour.

35. A solid pharmaceutical composition prepared by combining at least one pharmaceutically acceptable excipient with amorphous pimecrolimus of claim 1.

36. A method of treating a patient suffering from atopic dermatitis, comprising administering to the patient a therapeutically effective amount of the pharmaceutical composition of claim 35.

37. The amorphous pimecrolimus of claim 1, characterized by FT-IR spectroscopy by peaks at 2934, 2826, 1743, 1718, 1700, 1653, 1457, 1380, 1284, 1197, 1173, 1101, 1039, 988, 937, and 773 cm$^{-1}$.

38. The amorphous pimecrolimus of claim 1, characterized by a PXRD pattern substantially as depicted in FIG. 1, FIG. 6 or FIG. 11.

* * * * *

UNITED STATES PATENT AND TRADEMARK OFFICE
CERTIFICATE OF CORRECTION

PATENT NO.         : 7,589,100 B2
APPLICATION NO. : 11/293283
DATED              : September 15, 2009
INVENTOR(S)        : Kovacsne-Mezei et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 14 days.

Signed and Sealed this

Twenty-first Day of September, 2010

David J. Kappos
*Director of the United States Patent and Trademark Office*